United States Patent [19]

Johnson

[11] 4,350,446
[45] Sep. 21, 1982

[54] METHOD AND APPARATUS FOR CALORIMETRIC DIFFERENTIAL THERMAL ANALYSIS

[75] Inventor: Robert C. Johnson, Wilmington, Del.

[73] Assignee: E. I. Du Pont de Nemours and Company, Wilmington, Del.

[21] Appl. No.: 203,639

[22] Filed: Nov. 3, 1980

[51] Int. Cl.³ ............................................. G01K 17/00
[52] U.S. Cl. .................................................... 374/13
[58] Field of Search ........................... 73/15 B, 190 R

[56] References Cited

U.S. PATENT DOCUMENTS 3,059,471  10/1962  Calvet ...................................... 73/15
3,283,560  11/1966  Harden et al. ........................... 73/15
4,095,453   6/1978  Woo ........................................ 73/15

OTHER PUBLICATIONS

*Chemical Communications, Univ. of Stockholm,* "A Low Temperature DTA Apparatus for Simultaneous Measurement of Five Samples," 1975 Nr. 9 (Oct. 6)–T. Horlin, et al.
"In the Laboratory: Multiple Thermal Analyses," J. L. Kulp & Paul F. Kerr, *Science,* 105:413 (1947).
"Multiple Differential Thermal Analysis," *The American Mineralogist,* 33:387 (1948).
"Improved Differential Thermal Analysis Apparatus," J. Laurence Kulp & Paul F. Kerr, *American Mineralogist,* 34:839 (1949).
"Mineralogical Analysis of Soil Clays," Geologie en Munbouw, 16e Jaargang, pp. 69–83, Maart 1954.
"Differential Thermal Curves of Certain Hydrous and Anhydrous Minerals, with a Description of the Apparatus Used," *Economic Geology,* 45, 222–244 (1950).
"The Application of Differential Thermal Analysis at Constant Temperature to Evaluate Hazardous Thermal Properties of Chemicals," *Thermal Analysis,* vol. 1, 1969.

*Primary Examiner*—Herbert Goldstein

[57] ABSTRACT

A calorimetric differential thermal analyzer uses a planar thermoelectric sheet as its major heat flow path for transferring heat from a heat source to both the reference and sample positions. The heat source is connected to each of the positions by equivalent thermal paths formed by the sheet itself. These paths to each test position are made thermally equivalent by making them geometrically similar and forming isothermal boundaries on the sheet itself between each of the test positions. These isothermal boundaries are connected to the heat source and formed of a material having a high thermal conductance.

The thermal equivalency of the paths may be enhanced by removing portions of the sheetlike material to form well defined patterns of heat flow in the sheet; e.g., structures in which the sheet is formed into radial arms in a wheel-like array with each test position being on a different spoke of the wheel. Heat from the heat source may be applied through the hub of the wheel or the rim of the wheel or both, the hub and rim being in good thermal contact with isothermal boundaries having a high thermal conductance.

15 Claims, 12 Drawing Figures

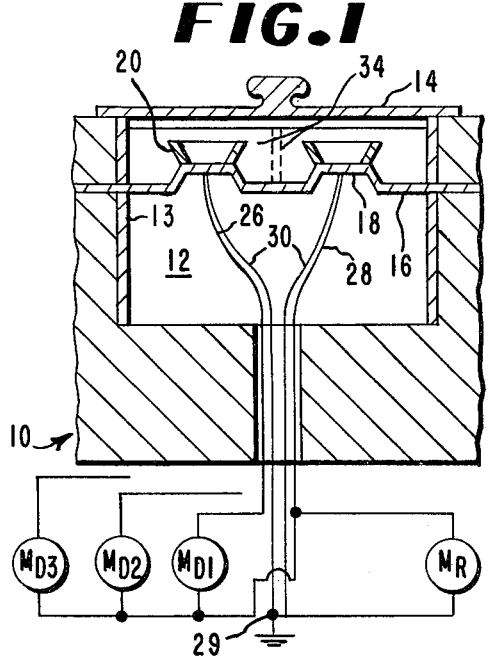
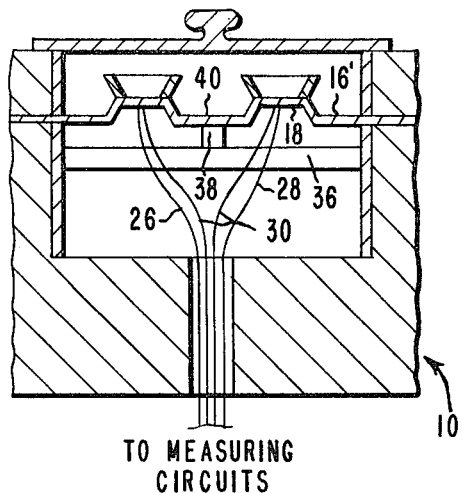
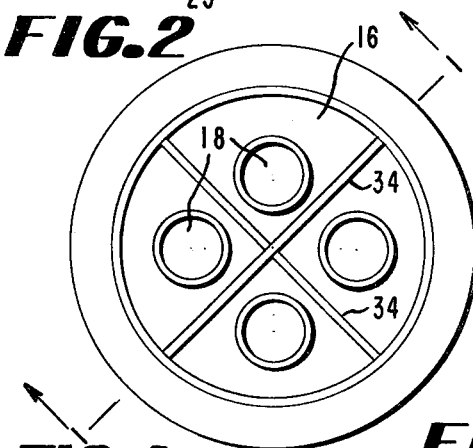
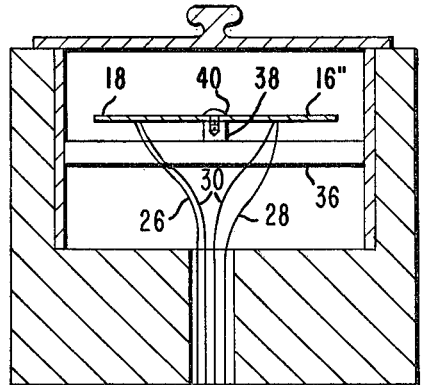
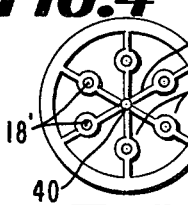
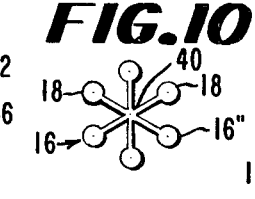
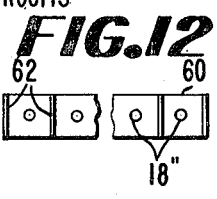
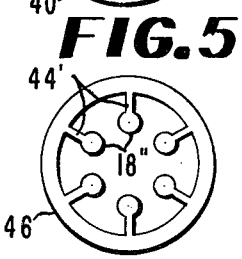
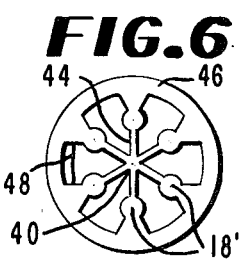
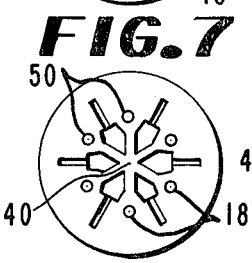
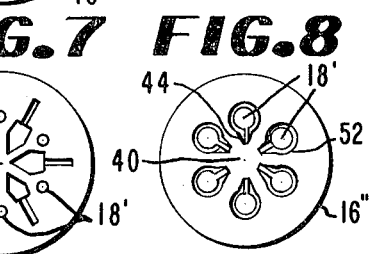

METHOD AND APPARATUS FOR CALORIMETRIC DIFFERENTIAL THERMAL ANALYSIS

BACKGROUND OF THE INVENTION

This invention relates to calorimetric differential thermal analyzers such as those described in U.S. Pat. Nos. 3,554,002 and 4,095,453 both assigned to E. I. duPont de Nemours and Company.

Differential thermal analyzers measure the difference between sample and reference material temperatures as their temperatures are varied. Differential scanning calorimeters (DSC) are differential thermal analyzers which give quantitative information about the samples by measuring heat flow to and from the samples. The calorimetric analyzers described in the two named patents use a heat flow type DSC cell. In this cell a thermoelectric disk, used to support both the sample and the reference material, serves as the major heat flow path for transferring heat to the sample and reference materials. The disk also is a common material of the differential thermocouple for measuring the difference in temperatures between the sample and reference materials. This thermoelectric disk is mounted inside a silver heating block having a silver lid. The sample and reference materials are placed in sealed metal pans so that the thermal environment is reproducible from run to run.

While instruments designed along these lines are extremely useful and have been very well received by the thermal analyst, they tend to suffer from their inability to run more than one sample at a time or to compare samples simultaneously in the same run. The construction and design of an instrument in which several samples can be run simultaneously is quite difficult because all test positions must be thermally equivalent. The reference should not bear any special relationship with any of the samples, and interchange between the sample and reference positions should result in a thermally equivalent structure. The presence of more than one sample can give rise to the serious problem of crosstalk, i.e., the appearance of a feature on the DSC curve for one sample caused by a thermal transition occurring at another sample position. This is highly undesirable and should be eliminated to the extent possible. To reduce crosstalk between samples, thermal communication between the positions of the samples or reference should be reduced to a low level.

Among the known multiple sample differential thermal analyzers (albeit not of the heat flow type), it has been customary to provide thermal isolation between each of the sample positions and the reference position. Such isolation may be accomplished by a thermal insulator such as a mica screen between each test position. Typical of these instruments is that described in the publication *Chemical Communications by the University of Stockholm* entitled "A Low Temperature DTA Apparatus for Simultaneous Measurement of Five Samples" by T. Horlin, T. Niklewski and M. Nygren, 1979 No. 9. This publication describes six symmetrically arranged holders, each thermally insulated from each other by means of a thin mica shield. However, this is not a heat flow type of instrument capable of giving quantitative information. Furthermore, since the effectiveness of all thermal insulation is relative, there is, in fact, crosstalk between the sample positions. Although tolerable in differential thermal analysis, significant crosstalk simply is not acceptable in differential scanning calorimetry.

SUMMARY OF THE INVENTION

In accordance with this invention, a cell for use in calorimetric differential thermal analysis comprises a unitary thermally conductive sheet fabricated to provide a plurality of test positions, at least one of the test positions being thermally connected with all other test positions by equivalent thermal paths formed by portions of the sheet, the sheet being formed of a material capable of forming one junction of a thermocouple, a heat source contacting the sheet to transfer heat through thermally equivalent paths in the sheet to each of the test positions, and means for forming with the sheet a thermocouple at each of the positions for measuring the relative temperatures of each position.

In one embodiment of this invention, elements of thermal conductance, higher than that provided by the sheet, contact one face of the sheet and are positioned symmetrically between each of the test positions to form an isothermal barrier there between. In another embodiment of the invention, the sheet defines a peripheral ring with the heat source continuously contacting the ring. In still another embodiment, the sheet defines distinct radial wheel-like arms extending to each test position, each test position being located in a circular array on the sheet and being thermally isolated not only by voids in the sheet between the spokes, but also by connecting the spokes to an isothermal region, i.e., a peripheral ring, a central hub or both.

When each of the test positions are thus isolated, there is reduced crosstalk between the several positions and greater structural rigidity of the disk, which in itself is believed to improve the signal to noise ratio of the output signals.

BRIEF DESCRIPTION OF THE DRAWINGS

Further advantages and features of this invention will become apparent upon consideration of the following description wherein:

FIG. 1 is a fragmentary cross-sectional, elevation view of a portion of a calorimetric differential thermal analysis cell constructed in accordance with this invention;

FIG. 2 is a plan view of the thermally conductive sheet, in the form of a thermoelectric disk, illustrated in FIG. 1;

FIG. 3 is a fragmentary cross-sectional elevation view of a portion of a calorimetric differential thermal analysis cell constructed in accordance with another embodiment of this invention in which the heat source is connected to the center of the thermoelectric disk;

FIGS. 4 through 8 inclusive illustrate different configurations that the thermoelectric disk may take when used in the embodiment of FIG. 3;

FIG. 9 is a fragmentary cross-sectional elevational view of a portion of a calorimetric differential thermal analysis cell constructed in accordance with still another embodiment of this invention;

FIG. 10 is a plan view of a thermoelectric disk that may be used in conjunction with the embodiment illustrated in FIG. 9;

FIG. 11 is a plan view of another configuration of a thermoelectric disk that may be used in the cell of FIG. 1; and FIG. 12 is a plan view of another configuration of a thermoelectric support that may be used in this invention.

DESCRIPTION OF THE PREFERRED EMBODIMENT

The calorimetric differential thermal analysis cell depicted in FIGS. 1 and 2 is a differential scanning calorimetric cell of the heat flow type. This heat flow type cell typically includes a heating block 10 (a metal block surrounded by a suitable heater, electric or otherwise—not shown). The heating block 10 defines a sample chamber 12, open at the top portion thereof and adapted to be closed by a suitable lid 14 illustrated schematically. Typically the heating block may be formed of a good thermal conductor such as copper and is lined with a tight-fitting element or innersleeve 13 which may be formed of an even better thermal conductor such as silver. The lid 14 may also be formed of silver and in practice may be in the form of a caplike cover, i.e., an annular sleeve with a closed end so as to fit over the entire cell block 10 such as is used in the Model 1090 Thermal Differential Scanning Calorimeter sold by E. I. duPont de Nemours and Company, Wilmington, Del. Typically the sleeve 13 is soldered to the block 10 to maintain good thermal contact.

Across the mid portion of the sample chamber 12, a thermoelectric disk 16 is disposed such that its peripheral portions are in good thermal contact with the silver sleeve 13 and block 10. Good thermal contact can be achieved by soldering with the peripheral portions of the disk being positioned between axial sections of the block. The thermoelectric disk 16 is in the form of a unitary disklike thermally conductive sheet fabricated to provide a plurality of thermal test positions 18 (each test position being preferably slightly raised to form a platform). One test position is reserved for an inert reference material while the remainder are sample test positions. Typically the platforms will support a sealed sample holder or cup 20 of known type. The sheet 16 preferably is formed of any suitable thermocouple forming material, preferably one having a high response to temperature changes such as Constantan. Any of the other known suitable thermoelectric or thermocouple materials such as chromel, alumel, etc. may also be used.

Leads or wires 26, 28 of a metal capable of forming a thermocouple junction with the metal of the sheet 16, are attached (using known techniques) to the mid-portion of each of the test positions 18. The wire 28 is connected to the reference position and the wires 26 are connected to each of the three illustrated sample test positions—only two connections are shown for clarity. These form, with the sheet, chromel-Constantan differential temperature monitoring thermocouples for measuring the temperature differences between the reference and each of the sample test positions 18 as represented by the meters $M_{D1}$, $M_{D2}$ and $M_{D3}$. Another lead wire 30, of a still different thermocouple forming metal, such as alumel, is attached so as to form thermocouple junctions with each of the lead wires 26, 28 at the points of attachment to the disk 16. As is well known, the thermocouple wires must be of sufficiently small cross section so as to minimize heat transfer from the test position.

This invention is based on the recognition that the heatflow to each reference position R and test position $S_1, S_2, S_3 \ldots S_N$ depends on the temperatures of the heat source boundaries (walls) with which each position is in thermal contact and the thermal resistances between each position and its boundaries. If the temperatures of the boundaries of each position and the thermal resistances between such boundaries and each test position are identical, then the heat transfer to each position depends only on the thermal behavior of its sample and not on the behavior of any other sample—in other words, there is no crosstalk.

The temperature of the boundaries of each position is made uniform (isothermal) and identical to all other position boundaries by constructing the boundary of a sufficient mass of a material of high thermal conductance. The thermal resistances are made identical by making each position's surroundings substantially geometrically identical.

In accordance with this invention, each of the test positions 18 are connected thermally with all other test positions and the heat source through equivalent thermal paths in the sheet itself. This is accomplished by forming each test position 18 to have the same geometrical configuration and placing isothermal boundaries between each of the sample and reference positions 18. The isothermal boundaries in the preferred embodiment of FIGS. 1 and 2 may be formed by a cross 34 soldered to the top of the sheet 16 symmetrically between each test position 18. This cross is soldered at its extreme ends to the wall of the silver sleeve 13 which forms the outer thermal boundary and hence assumes a temperature closely approximating that of the heat source. In this way the isothermal boundary formed by the cross and the heat source 13 separates each of the test positions into substantially identical compartments, i.e., the paths of heat transfer between test position and heat source are thermally equivalent. The cross may be formed of silver or other high thermal conductivity material in a manner which in any case results in a boundary which has a lower, preferably much lower, thermal resistance, i.e., its thermal conductance is higher, than that of the sheet 16.

This results in reduced crosstalk and a greater structural rigidity of the disk which is believed to improve the signal to noise ratio and provides the possibility of using different atmospheres in each sample and reference compartment. Because of the use of plural samples, there is an increased sample throughput and a better basis for intercomparison of data because all samples can be run under identical conditions. Further, reference sample materials can be included for quality control and temperature or transition heat standards may be included for calibration purposes.

In alternative embodiments of this invention depicted in FIGS. 3 and 4, the sample cell is constructed essentially in the same manner as described in connection with FIGS. 1 and 2 with the exception that the isothermal boundaries and thermally equivalent paths have a different configuration. Thus, in FIGS. 3 and 4, the isothermal boundary between the several test and reference positions—in this case five sample test positions are shown—is provided by connecting a member having a high thermal conductance such as copper or silver in the form of a bar 36 to the heat source, i.e., the sleeve 13, the bar being soldered at either end of the sleeve. A stud 38 at the center portion of the bar is soldered to the center of the disklike sheet 16'. The bar in this case may be formed of a copper member 0.049 inch thick and 0.200 inch high which has been found suitable for use with the Du Pont Model 1090 series differential scanning calorimeter.

In accordance with this invention, the sample positions 18' are formed along distinct radial arms 44 extending from the center of the disk 40 through each of the test positions 18' to the rim of the disk and the heat source. Any one of the test positions may be selected as the reference position. In this instance, the test positions are located symmetrically in a circular pattern concentric within the test chamber. The disklike sheet 16' may be formed in various methods. They may be etched by using known techniques (using photoresist material and phototools to provide desired pattern) to remove portions 42 of the thermoelectric sheet 16 between the radial arms 44 leaving a wheel-like structure. Alternatively the wheel-like structure may be formed using a screen to print thick film thermoelectric conductor compositions and firing to form the disks. In either case the peripheral or circumferential portion (corresponding to the rim of the wheel) 46 contacts (and is soldered or brazed to) the heat source 13 and the spokes of the wheel formed by the radial arms 44 provides heat transfer paths both from the center 40 (the hub) and from the circumference or rim 46 to each the sample positions 18'. These arms thus provide equivalent thermal paths to each test position 18', sample as well as reference, because each of the radial arms are joined together at the isothermal boundary provided by the hub 40 and extend out to the similar isothermal boundary provided by the rim 46.

Thus all possible heat flow paths to and from each test position 18' are through the arms 44 to points of the same temperature. Since all the sample and reference positions are connected between the same temperature points they are therefore thermally equivalent positions. This has the great advantage of reducing crosstalk between the samples, i.e., thermal events occurring on one sample essentially are totally isolated from that occurring on those of another sample and from the reference position.

Alternative embodiments of this invention that may be used with the configuration of FIG. 3 are depicted in the various etch patterns depicted in FIGS. 5 to 7. Thus, in the pattern depicted in FIG. 5, there is no contact with the center, there being only a radial inward feed from the rim 46 (which is in thermal communication with the heat source 13) to the various test positions 18". The embodiment of FIG. 6, somewhat analogous to that of FIG. 4, provides an enlarged outer peripheral portion 48 of each arm 44 to afford better heat transfer. A central isothermal point 40 is provided in this embodiment as it is provided in the embodiments of FIGS. 7 and 8. In FIG. 7 a still greater circumferential transfer of heat is provided by the sectors 50 from the heat source 13.

Further embodiments of the invention are depicted in FIGS. 8, 9, and 10 in which disk-like sheets 16" may be formed to have a smaller diameter than that of the test chamber 12 such that the support for the thermal feed for the test positions is that provided entirely through the hub of the disk by the stud 38. In this case the disklike sheet may assume the configuration depicted in FIGS. 8 or 10 having plural radial arms extending outwardly from the center position 40, which thermally contacts the stud 38 and is soldered thereto as described previously, hence the stud 38 thermally feeds the various sample positions 18. In the FIG. 8 embodiment, the disk 16" is essentially solid with small circular portions 52 removed to define the test positions 18' each supported by a radial arm 44.

Still another alternative embodiment of the invention is depicted in FIG. 11. The embodiment of FIG. 11 is an annular disk 16' that may be used in the cell of FIG. 1. In this case, however, the isothermal bars 34' are thermally in contact with the sleeve heat source 13 and extend radially inwardly only part way to the extent of the annulus of the sheet 16'. As before in every embodiment of the invention, a thermocouple pair 26 or 28 and 30 are connected to form a thermocouple at each test position.

The embodiment of FIG. 12 is somewhat different in configuration in that a linear array of test positions 18''' is shown formed on a rectangular sheet 60 of thermocouple forming material. Isothermal bars 62 of a good thermal conductivity material are secured as by soldering to the top of the sheet 60 to divide the sheet into equal area test positions 18'''. Each bar preferably has each end in good thermal contact, as previously described, with a heat source (not shown). In this case, the chamber would be differently configured, i.e., a rectangular oven chamber would be used.

There has thus been described a relatively simple differential scanning calorimeter in which multiple samples may be simultaneously analyzed by using the apparatus or method of this invention. The crosstalk between sample positions is reduced and in most cases a greater structural rigidity is achieved.

I claim:

1. A cell for use in a differential scanning calorimeter comprising:
   a unitary thermally conductive sheet formed of a material capable of forming a junction of a thermocouple and fabricated to provide a plurality of thermal test positions, at least one of said test positions being thermally connected with all other test positions by equivalent thermal paths of said sheet,
   a heat source having portions contacting said sheet to transfer heat between said source and each of said test positions through thermally equivalent paths in said sheet, and
   means for forming with said sheet a thermocouple at each of said positions for measuring the relative temperatures at each position.

2. The apparatus of claim 1 wherein the thermal conductance of said portions is higher than the thermal conductance of said paths, said portions contacting one face of said sheet between each pair of said test positions.

3. The apparatus of claim 2 wherein said portions are intercontacted with each other and extend transversely of said sheet to form a chamber-like region at each test position.

4. The apparatus of claim 1 or 2 wherein said sheet is disk-like, said heat source is annular in configuration and contacts the periphery of said sheet, said portions extending linearly as radii of a circle between different positions on said heat source.

5. The apparatus of claim 1 wherein said sheet defines distinct radial arms extending to each said test position, each test position being located in a circular array on said sheet and being thermally isolated along the circular dimension by voids in said sheet.

6. The apparatus of claim 5 wherein said sheet defines a peripheral ring and said heat source is annular in configuration and continuously contacts said ring.

7. The apparatus of claim 6 wherein said radial arms extend only between said ring and said test positions.

8. The apparatus of claim 6 wherein said arms are continuous between said ring and the center of said test positions.

9. The apparatus of claim 8 which includes a piece of material having a thermal conductance greater than that of said sheet thermally connected between said heat source and the center of said test positions.

10. The apparatus of claim 5 wherein said radial arms extend only inwardly from each test position to the center of said circular array, said heat source thermally connected only to said center by a piece of material having a thermal conductivity greater than that of said sheet.

11. The apparatus of claim 3 wherein said sheet is annular in configuration.

12. The apparatus of claim 3 wherein said sheet is rectangular in configuration.

13. A method for the simultaneous calorimetric differential thermal analysis of plural substances, comprising the steps of:

placing quantities of said substances in two of three different receptacles located on a unitary thermally conductive sheet of a first metal, applying heat to each of said test positions through separate, equivalent thermal paths formed in said sheet, and measuring the differential changes in temperature between the third receptacle and each of said different receptacles.

14. The method of claim 13 wherein the additional step of forming on said sheet thermal boundaries of a material having a higher thermal conductance than said sheet.

15. The method of claim 14 where said equivalent thermal paths are formed by removing portions of said sheet in a symmetrical pattern to form radial thermal paths.

* * * * *